United States Patent [19]

Hang

[11] Patent Number: 4,963,486
[45] Date of Patent: Oct. 16, 1990

[54] **DIRECT FERMENTATION OF CORN TO L(+)-LACTIC ACID BY *RHIZOPUS ORYZAE***

[75] Inventor: Yong D. Hang, Geneva, N.Y.

[73] Assignee: Cornell Research Foundation, Inc., Ithaca, N.Y.

[21] Appl. No.: 342,207

[22] Filed: Apr. 21, 1989

[51] Int. Cl.$^5$ .................... C12P 7/56; C12R 1/845
[52] U.S. Cl. .................................... 435/139; 435/939
[58] Field of Search .............................. 435/139, 939

[56] References Cited

U.S. PATENT DOCUMENTS 2,132,712 10/1938 Ward et al.
3,125,494 3/1964 Snell et al.
4,564,594 1/1986 Goldberg et al.

FOREIGN PATENT DOCUMENTS 51-012090 1/1976 Japan.
53-113085 10/1978 Japan.
60-006196 1/1985 Japan.

OTHER PUBLICATIONS

Article by Doris Wolf (Finger Lakes Times, Geneva, N.Y., Jan. 23, 1989), discusses various products obtainable from corn.
Industrial Microbiology, 3rd ed. (McGraw-Hill, N.Y., 1959, Chapter 34, pp. 630-636.
Chan Jo Kim et al., Sanop Misdenamul Hakhoechi, vol. 13, No. 4, pp. 329-337 (1985).
Kanel, E. Microbiologiia 3:2 pp. 259-265 (1934).
Hang, Y. D. et al., Biotechnology Letters, 11(2):119-120 (1989).
Dubois, Mickel et al., Anal. Chem., 28:350-356 (1956).
Yang "Direct Fermentation of Corn to L(+) lactic acid by *Rhizopus oryzae*" Biotech Letters, vol. 11, No. 4 (1989), pp. 299-300.
Yu et al., Biotech Letters, vol. 11, No. 8 (1988), pp. 597-600.

*Primary Examiner*—Herbert J. Lilling
*Attorney, Agent, or Firm*—Jones, Tullar & Cooper

[57] ABSTRACT

L(+)-lactic acid is produced in high yield by a direct one step fermentation of renewable biomass such as ground corn using *Rhizopus oryzae* in the presence of calcium carbonate. A kilogram of crushed corn yields over 350 grams high purity L(+)-lactic acid.

7 Claims, No Drawings

DIRECT FERMENTATION OF CORN TO L(+)-LACTIC ACID BY RHIZOPUS ORYZAE

BACKGROUND OF THE INVENTION

For the past several years, the producers of raw agricultural commodities have suffered from low prices and surpluses because of reduced demand and increased world supplies (ESCOP. 1988. Enhanced research agenda for value added food and non-food uses of agricultural products. The Experiment Station Committee on Organization and Policy. Washington, D.C.). Recently efforts have been made to reverse the trend by converting agricultural commodities into value-added products. For example, corn was grown in the 1970's mainly for livestock feeds, but today it is being used increasingly to produce high-fructose corn syrup, fuel-alcohol and other non-food products (Wolf, D. Finger Lakes Times, Geneva, N.Y.: Jan. 23, 1989).

Lactic acid is produced commercially by the fermentation of glucose, molasses or cheese whey with homo-fermentative lactic acid bacteria (Prescott, S. C. et al, 1959, Industrial Microbiology, 3rd ed. New York: McGraw-Hill). Wart et al, U.S. Pat. No. 2,132,712 have produced dextro-lactic acid by fermentation of glucose solutions with Rhizopus oryzae.

It is desired to produce a L(+)-lactic acid in high yield and purity in a direct one-step fermentation from a readily renewable biomass. L(+)-lactic acid and its salts will find increased use as components of foods, pharmaceuticals and as monomer in the preparation of biodegradeable polymers.

The instant invention relates to the simultaneous saccharification and fermentation of corn to L(+)-lactic acid in high yield.

BRIEF DESCRIPTION OF THE INVENTION

One object of the invention is a process for producing L(+)-lactic acid which comprises fermenting a plant-starch-containing renewable biomass, selected from the group consisting of a cereal grass seed or kernel, an edible starchy root or an edible starchy tuber, in a single step fermentation in the presence of an L(+)-lactic acid producing amount of Rhizopus oryzae to produce L(+)-lactic acid and isolating L(+)-lactic acid or a salt thereof.

Another object of the invention is a direct single step fermentation process to convert corn and other cereal grass seeds or kernels directly to L(+)-lactic acid without requiring either an intermediate hydrolysis or separate enzyme hydrolysis to first convert the polysaccharide biomass to sugars prior to fermenting said sugars.

DESCRIPTION OF THE INVENTION

It has now been found that L(+)-lactic acid can be produced in high yield by a direct single step fermentation of a renewable biomass such as corn using Rhizopus oryzae. Rhizopus oryzae NRRL 395 ATCC 9363 is particularly efficacious in producing L(+)-lactic acid in yields of greater than 44% based on consumed carbohydrate as glucose. A kilogram of crushed corn yields over 350 grams of L(+)-lactic acid.

A preferred process for producing L(+)-lactic acid using corn as the renewable biomass substrate comprises mixing the ground corn with water at a temperature of from about 60° C. to about 120° C. for a time sufficient to form a gelatinous mass. Thereafter, the Rhizopus oryzae fungus mold is added in an amount, from about 1 to about 12 percent basis 100 parts fermentation gel, sufficient to effect saccharification and direct fermentation to L(+)-lactic acid in high yield. After gelatinization of the renewable biomass an acid-neutralizing material is added to maintain the pH of the reaction mixture in the slightly acidic to neutral range. Although other bases may be used for neutralization of the formed acid, calcium carbonate is preferred. The preferred range of pH is from about 4.0 to 7.2. Useful temperatures for the fermentation process is from about 20° C. to about 40° C. and preferably about 30° C. Other neutralization agents can be used in place of the calcium carbonate. These include sodium carbonate, ammonium carbonate, potassium carbonate, sodium hydroxide, potassium hydroxide and ammonium hydroxide. Calcium carbonate is a preferred material because of the special solubility properties of the calcium salt of L(+)-lactic acid formed. From a solution of calcium salt of from about 6 to 12 weight percent calcium L(+)-lactate precipitates nicely at about 4° C. thus providing a convenient means of isolating the product in high purity. When further purity is needed, the salt can be recrystallized from aqueous solution. Neutralization readily affords the free acid.

The process is a one-step direct saccharification and fermentation process since it does not include a separate preliminary hydrolysis step as required in other processes where starch must first be transformed by acid or enzymatic hydrolysis (usually by a different enzyme) into a fermentable sugar. The invention requires no other added organism or enzyme. Rhizopus oryzae is unique in that it is capable of supplying all of the required enzymes needed for both saccharification and fermentation to L(+)-lactic acid. Similarly no extraneous nutrients or minerals need to be added since these are present in the renewable biomass.

Plant-starch-containing renewable biomass, the starting material for the invention, is converted in a one-step fermentation process to L(+)-lactic acid in high yield. For purposes of this invention, the terms "renewable biomass" of "plant-starch-containing renewable biomass" means a food source which contains the polysaccharide starches which serve as nutritional reservoirs in plants and vegetables. Such biomass includes, for example, cereal grass seeds or kernels, edible starchy roots, edible starch tubers and the like. The biomass starches are different and distinct from cellulose. Cellulose have adjacent glucose fragments linked to each other in 1,4-$\beta$-linkage whereas the plant cell starches have 1,4-$\alpha$-linkages and the repeating disaccharide unit is not cellubiose but maltose. For the purpose of distinguishing the plant-starch-containing renewable biomass used as a starting material in the one-step fermentation process of this invention, reference is made to Chapter 4, Chemistry of Carbohydrate, McGraw Hill 1959, which is incorporated herein by reference.

Other renewable readily available biomass sources of high carbohydrate content can be substituted for the ground corn. Such substrate include, for example, sorghum, rice, barley, cassava, wheat, milo, barley, rye, oat, potato, sweet potato, Jerusalem artichoke, and the like. Other useful substrates include potato waste materials, grape juice, grape pomace, apple pomace, and raisins. Ground corn is the preferred substrate. Corn and the above noted renewable biomass are advantageous because they do not need to be treated with enzyme or acid to first hydrolyze the starches to glucose as is necessary in other processes such as the formation of ethanol by yeast.

There follows a number of examples which are to be considered illustrative rather than limiting. All parts and percentages are by weight and all temperatures are degrees centigrade unless otherwise specified.

EXAMPLES 1-8

Substrate: The corn used in this study was a corn purchased from a local supply house and contained about 80% fermentable sugar as glucose.

Cultures: The culture used in this work was a lactic acid-producing strain of R. oryzae NRRL 395 obtained from Dr. C. W. Hesseltine, Northern Regional Research Center, USDA, Peoria, Ill. The strain was maintained on potato dextrose agar slants. Conidia of the mold were produced on steamed rice by the method of Wang, H. L. et al, *J. Food Sci.*, 40:168-170 (1975), L(+)-lactic acid production experiments were conducted as follows: 15 g of ground corn plus 100 ml of distilled water were added to 500 ml Erlenmeyer flasks and sterilized at 121° C. for 15 minutes. Each flask was inoculated with $2 \times 10^7$ viable spores and incubated at 30° C. for 96 hours on a New Brunswick gyratory shaker operated at a speed of 240 RPM. Sterile calcium carbonate (5 g) was added to each flask approximately 24 hours after inoculation. At the end of the fermentation, the fermented materials were centrifuged and supernatants were analyzed for L(+)-lactic acid and residual carbohydrate.

It is recognized that various strains of *Rhizopus oryzae*, such as for example ATCC 9363, will be useful in the one step fermentation of the biomass substrate listed above. *Rhizopus oryzae* NRRL 395 (ATCC 9363) is a preferred organism for the direct conversion to L(+)-lactic acid.

Total carbohydrate was determined as glucose by the phenol sulfuric acid method of (Dubois, M. et al, *Anal. Chem.*, 28:350-356 (1956)). L(+)-lactic acid was analyzed with a Rabbit HPLC unit using a Bio-Rad Aminex HPX-87C column (Hang et al, *Biotechnol. Lett.*, 2:119-120 (1989)).

RESULTS

Table 1 shows the results of simultaneous saccharification and fermentation of ground corn to L(+)-lactic acid by *R. oryzae* NRRL 395. The amount of L(+)-lactic acid produced ranged from approximately 303 g to 390 g per kg of corn fermented and the mean value of the eight different lactic acid fermentation experiments was calculated to be more than 354 g per kg of corn. *R. oryzae* reduced the carbohydrate content from an initial value of greater than 818 g to nearly 17 g per kg of corn in 96 hours, representing a consumption of approximately 98%. The average yield of L(+)-lactic acid was found to be more than 44% on the basis of the amount of total carbohydrate as glucose consumed. The results of the present investigation were thus comparable to those of an earlier report (Lockwood et al 1936) that *R. oryzae* yielded about 43% when grown in a chemically defined medium with D-glucose as the sole carbon source.

TABLE 1

Direct fermentation of corn to L(+)-lactic acid by *R. oryzae* NRRL 395

| Example | Yield of L(+)-lactic acid (g/kg) | Residual carbohydrate as glucose (g/kg) |
|---|---|---|
| 1 | 390.0 | 13.3 |
| 2 | 384.0 | 13.7 |
| 3 | 322.7 | 20.5 |
| 4 | 360.7 | 18.5 |

TABLE 1-continued

Direct fermentation of corn to L(+)-lactic acid by *R. oryzae* NRRL 395

| Example | Yield of L(+)-lactic acid (g/kg) | Residual carbohydrate as glucose (g/kg) |
|---|---|---|
| 5 | 348.7 | 13.5 |
| 6 | 346.0 | 13.3 |
| 7 | 383.3 | 16.8 |
| 8 | 302.7 | 25.2 |
| Standard Deviation | 31.2 | 4.34 |
| Mean | 354.8 | 16.9 |

Initial carbohydrate as glucose 818.5 g/kg corn

EXAMPLE 9

Repeating the experiment of Example 1, but substituting *R. oryzae* NRRL 394 for the *R. oryzae* NRRL 395, will produce L(+)-lactic acid product in a yield slightly less than shown in the example of Table 1.

EXAMPLES 10-13

The process of Examples 1-8 was repeated using oat, rice, wheat and raisins in place of the ground corn. As shown in Table 2, satisfactory yields of L(+)-lactic acid were produced.

TABLE 2

Direct Fermentation of Oat, Rice, Wheat and Raisins to L(+)-Lactic Acid by *Rhizopus oryzae* NRRL 395

| Example | Substrate | Yield of L(+)-Lactic acid (g/kg) |
|---|---|---|
| 10 | Oat | 210 |
| 11 | Rice | 437 |
| 12 | Wheat | 153 |
| 13 | Raisin | 433 |

EXAMPLE 14

Repeating the process of Examples 1-8, but substituting barley, sorghum, milo, potato and cassava in place of the ground corn, will produce L(+)-lactic acid in satisfactory yields.

What is claimed is:

1. A single-step fermentation process for producing L(+)-lactic acid in high yield without the addition of starch-to-sugar converting enzyme substantially from a plant starch, serial grass or kernel renewable biomass selected from the group consisting of corn cassava, rice, oat, wheat, barley and sorghum which comprises:
   (a) heating the finely divided biomass with water at a temperature of from about 60° C. to about 124° C. for a time sufficient to sterilize the said biomass and to form a gelatinous medium;
   (b) inoculating the gelatinous medium with viable spores of L(+)-lactic acid producing *Rhizopus oryzae* and fermenting the medium at a temperature from about 20° C. to about 40° C;
   (c) adding sterile neutralizing material to the medium after about 24 hours incubation to maintain the pH of the medium in the range of from about 4.0 to about 7.2;
   (d) further incubating to produce (L(+)-lactic acid or salt thereof in high yield; and
   (e) isolating the L(+)-lactic acid wherein the said process is conducted on the substantial absence of extraneous nutrients or minerals.

2. The process of claim 1 wherein the *Rhizopus oryzae* is NRRL 395 having an ATCC No. 9363.

3. The process of claim 1 wherein the renewable biomass is corn.

4. The process of claim 1 wherein the biomass is rice.

5. The process of claim 1 wherein the biomass is barley.

6. The process of claim 1 wherein the biomass is cassava.

7. L(+)-lactic acid prepared according to the process of claim 3.

* * * * *